(12) United States Patent
Lauks et al.

(10) Patent No.: US 9,753,003 B2
(45) Date of Patent: *Sep. 5, 2017

(54) DIAGNOSTIC DEVICES INCORPORATING FLUIDICS AND METHODS OF MANUFACTURE

(71) Applicant: EPOCAL INC., Ottawa (CA)

(72) Inventors: Imants Lauks, Ottawa (CA); Andrzej Maczuszenko, Etobicoke (CA)

(73) Assignee: Epocal Inc., Ottawa (CA)

( * ) Notice: Subject to any disclaimer, the term of this patent is extended or adjusted under 35 U.S.C. 154(b) by 917 days.

This patent is subject to a terminal disclaimer.

(21) Appl. No.: 13/923,845

(22) Filed: Jun. 21, 2013

(65) Prior Publication Data
US 2013/0277215 A1    Oct. 24, 2013

Related U.S. Application Data

(60) Division of application No. 12/870,463, filed on Aug. 27, 2010, now Pat. No. 8,506,778, which is a (Continued)

(51) Int. Cl.
*G01N 27/327* (2006.01)
*G01N 27/26* (2006.01)
(Continued)

(52) U.S. Cl.
CPC .......... *G01N 27/26* (2013.01); *B01L 3/50273* (2013.01); *B01L 3/502707* (2013.01);
(Continued)

(58) Field of Classification Search
CPC ..... G01N 2035/00148; G01N 27/3272; G01N 27/327; G01N 27/416; G01N 2021/0193;
(Continued)

(56) References Cited

U.S. PATENT DOCUMENTS 4,062,750 A    12/1977  Butler
4,133,735 A    1/1979   Afromowitz
(Continued)

FOREIGN PATENT DOCUMENTS

EP    0325562    7/1989
EP    0352691    1/1990
(Continued)

OTHER PUBLICATIONS

Matysik et al., "A Disposable Electrode Based on Zeolite-Polymer Membranes for Potentiometric Titrations of Ionic Surfactants", Sens Actuators, B. Chem; Sensors and Actuators, B: Chemical, Jun. 20, 2002, vol. 85, No. 1-2, pp. 104-108.
(Continued)

*Primary Examiner* — Alexander Noguerola
(74) *Attorney, Agent, or Firm* — Borden Ladner Gervais LLP (57) ABSTRACT

The present invention relates to diagnostic devices incorporating electrode modules and fluidics for performing chemical analyzes. The invented devices consist of at least one component sensor formed on an electrode module, the sensor being contained within a fluidic housing. The electrode module is a laminate of a perforated epoxy foil and a photo-formed metal foil with sensor membranes deposited into the perforations. The fluidic housing is a diagnostic card consisting of a plastic card-like body, the at least one component sensor, a sealed chamber defined in the card body for containing a fluid, a fluid conduit for fluidically connecting the chamber with the sensor region, a valve for fluidically connecting the chamber to the fluid conduit, and a delivery structure separate and distinct from the valve for forcing fluid from the chamber and into the fluid conduit.

19 Claims, 6 Drawing Sheets

Related U.S. Application Data continuation of application No. 10/856,782, filed on Jun. 1, 2004, now Pat. No. 7,842,234, which is a continuation-in-part of application No. 10/307,481, filed on Dec. 2, 2002, now Pat. No. 7,094,330.

(51) Int. Cl.
    *B01L 3/00*     (2006.01)
    *G01N 27/403*     (2006.01)
    *G01N 21/01*     (2006.01)
    *G01N 35/00*     (2006.01)
    *B01L 7/00*     (2006.01)

(52) U.S. Cl.
CPC ... *B01L 3/502715* (2013.01); *B01L 3/502723* (2013.01); *B01L 3/502738* (2013.01); *G01N 27/3272* (2013.01); *G01N 27/403* (2013.01); *B01L 7/00* (2013.01); *B01L 2200/025* (2013.01); *B01L 2200/0689* (2013.01); *B01L 2200/148* (2013.01); *B01L 2200/16* (2013.01); *B01L 2300/0645* (2013.01); *B01L 2300/0816* (2013.01); *B01L 2300/0887* (2013.01); *B01L 2300/1805* (2013.01); *B01L 2300/1827* (2013.01); *B01L 2400/0481* (2013.01); *B01L 2400/0487* (2013.01); *B01L 2400/0683* (2013.01); *G01N 2021/0193* (2013.01); *G01N 2035/00148* (2013.01)

(58) Field of Classification Search
CPC ... G01N 21/01; G01N 21/05; G01N 2021/058
See application file for complete search history.

(56) References Cited

U.S. PATENT DOCUMENTS

| | | | |
|---|---|---|---|
| 4,225,410 A | 9/1980 | Pace | |
| 4,276,141 A | 6/1981 | Hawkins | |
| 4,301,412 A | 11/1981 | Hill | |
| 4,342,964 A | 8/1982 | Diamond | |
| 4,431,508 A | 2/1984 | Brown | |
| 4,436,610 A | 3/1984 | Enzer | |
| 4,484,987 A | 11/1984 | Gough | |
| 4,534,356 A | 8/1985 | Papadakis | |
| 4,551,209 A | 11/1985 | Lauks | |
| 4,592,824 A | 6/1986 | Smith | |
| 4,604,303 A | 8/1986 | Takakura et al. | |
| 4,613,422 A | 9/1986 | Lauks | |
| 4,629,424 A | 12/1986 | Lauks | |
| 4,654,127 A | 3/1987 | Baker | |
| 4,682,602 A | 7/1987 | Prohaska | |
| 4,689,309 A | 8/1987 | Jones | |
| 4,734,184 A | 3/1988 | Burleigh | |
| 4,739,380 A | 4/1988 | Lauks | |
| 4,864,229 A | 9/1989 | Lauks | |
| 4,877,528 A | 10/1989 | Friesen | |
| 4,933,048 A | 6/1990 | Lauks | |
| 4,954,087 A | 9/1990 | Lauks | |
| 5,008,616 A | 4/1991 | Lauks | |
| 5,009,766 A | 4/1991 | Lauks | |
| 5,030,310 A | 7/1991 | Wogoman | |
| 5,063,081 A | 11/1991 | Cozzette | |
| 5,078,854 A | 1/1992 | Burgess | |
| 5,096,669 A * | 3/1992 | Lauks | B01L 3/502707 204/403.02 |
| 5,112,455 A | 5/1992 | Cozzette | |
| 5,124,661 A | 6/1992 | Zelin | |
| 5,141,868 A | 8/1992 | Shanks | |
| D332,833 S | 1/1993 | Lauks | |
| 5,183,549 A | 2/1993 | Joseph | |
| 5,200,051 A | 4/1993 | Cozzette | |
| 5,212,050 A | 5/1993 | Mier | |
| D337,164 S | 7/1993 | Lauks | |
| 5,246,576 A | 9/1993 | Leader | |
| 5,325,853 A | 7/1994 | Morris | |
| 5,385,659 A | 1/1995 | Gumbrecht | |
| 5,416,026 A | 5/1995 | Davis | |
| 5,445,920 A | 8/1995 | Saito | |
| 5,447,440 A | 9/1995 | Davis | |
| 5,466,575 A | 11/1995 | Cozzette | |
| 5,496,521 A | 3/1996 | Leiner | |
| 5,514,253 A | 5/1996 | Davis | |
| 5,531,870 A | 7/1996 | Cha | |
| 5,554,272 A | 9/1996 | Benco | |
| 5,554,339 A | 9/1996 | Cozzette | |
| 5,593,638 A | 1/1997 | Davis | |
| 5,605,664 A | 2/1997 | Lauks | |
| 5,609,824 A | 3/1997 | Lauks | |
| 5,614,416 A | 3/1997 | Lauks | |
| 5,628,961 A | 5/1997 | Davis | |
| 5,638,828 A | 6/1997 | Lauks | |
| 5,653,243 A | 8/1997 | Lauks | |
| 5,658,444 A | 8/1997 | Black | |
| 5,666,967 A | 9/1997 | Lauks | |
| 5,708,247 A | 1/1998 | McAleer | |
| 5,726,026 A * | 3/1998 | Wilding | B01D 67/0062 366/DIG. 3 |
| 5,727,548 A | 3/1998 | Hill | |
| 5,779,650 A | 7/1998 | Lauks | |
| 5,789,253 A | 8/1998 | Lauks | |
| 5,821,399 A | 10/1998 | Zelin | |
| 5,837,446 A | 11/1998 | Cozzette | |
| 5,837,454 A | 11/1998 | Cozzette | |
| 5,900,215 A | 5/1999 | Seifert | |
| 6,010,463 A | 1/2000 | Lauks | |
| 6,030,827 A | 2/2000 | Davis | |
| 6,241,862 B1 | 6/2001 | McAleer et al. | |
| 6,306,594 B1 | 10/2001 | Cozzette | |
| 6,379,883 B2 | 4/2002 | Davis | |
| 6,432,296 B1 | 8/2002 | Daniel | |
| 6,438,498 B1 | 8/2002 | Opalsky | |
| 6,451,191 B1 | 9/2002 | Bentsen et al. | |
| 6,484,045 B1 | 11/2002 | Holker | |
| 6,750,053 B1 | 6/2004 | Opalsky | |
| 6,766,817 B2 | 7/2004 | da Silva | |
| 7,074,610 B2 | 7/2006 | Cozzette | |
| 7,087,149 B1 | 8/2006 | Muguruma | |
| 7,208,077 B1 | 4/2007 | Albers et al. | |
| 7,842,234 B2 * | 11/2010 | Lauks | B01L 3/502707 204/400 |
| 2002/0011408 A1 | 1/2002 | Lee | |
| 2002/0177958 A1 | 11/2002 | Opalsky | |
| 2002/0179444 A1 | 12/2002 | Lauks | |
| 2003/0148530 A1 | 8/2003 | Lauks | |
| 2003/0170881 A1 | 9/2003 | Davis | |
| 2004/0018577 A1 | 1/2004 | Campbell | |
| 2004/0175296 A1 | 9/2004 | Opalsky | |
| 2005/0054078 A1 | 3/2005 | Miller | |
| 2005/0133368 A1 | 6/2005 | Davies et al. | |
| 2006/0046275 A1 | 3/2006 | Collier | |
| 2006/0160164 A1 | 7/2006 | Miller | |
| 2007/0015977 A1 | 1/2007 | McCann | |

FOREIGN PATENT DOCUMENTS

| | | |
|---|---|---|
| EP | 0551769 | 7/1993 |
| EP | 1087225 | 3/2001 |
| EP | 1193495 | 4/2002 |
| GB | 1584788 | 2/1981 |
| JP | 51-113788 | 10/1976 |
| JP | 2087067 | 3/1990 |
| JP | 02-144130 | 6/1990 |
| JP | 03-505783 | 12/1991 |
| JP | 06-018476 | 1/1994 |
| JP | 9299445 | 11/1997 |
| JP | 11083783 | 3/1999 |
| JP | 2003-515133 | 4/2003 |
| JP | 2004-532421 | 10/2004 |
| RO | 81891 | 5/1983 |
| WO | 0003222 A2 | 1/2000 |
| WO | 0058720 | 10/2000 |
| WO | 0062048 A2 | 10/2000 |
| WO | 0063685 | 10/2000 |

(56) References Cited

FOREIGN PATENT DOCUMENTS

| WO | 03034056 | 4/2003 |
|---|---|---|
| WO | 03/100083 A1 | 12/2003 |
| WO | 2004051251 | 6/2004 |

OTHER PUBLICATIONS

Sinsabaugh et al., "A Batch-Processed Reference Micro Electrode Integrated on a Silicon Substrate", Department of Electrical Engineering & Applied Physics and Electronics Design Center, vol. 86, Issue 14, 1986, pp. 66-73.
Janata et al., "Solid State Chemical Sensors", 1985, pp. 101-103.
Japanese Patent Application No. 513633/2007, Office Action dated May 19, 2009.
Japanese Patent Application No. 513633/2007, Office Action dated Nov. 17, 2009.
Japanese Patent Application No. 2004-555906, Office Action dated Dec. 1, 2009.
European Patent Application No. 05749838.8, European Search Report dated Aug. 21, 2012.
U.S. Appl. No. 12/819,273, Office Action dated Nov. 23, 2012.
U.S. Appl. No. 12/819,273, Office Action dated Jul. 22, 2013.
Lutz et al. "Water Absorption and Water Vapor Permeation Characteristics of HTV Silicone Rubber Material", Electrical Insulation (ISEI), Conference Record of the 2012 IEEE International Symposium, Jun. 10-13, 2012, p. 481-482.
Oksanen et al. "Molecular Mobility in Mixtures of Absorbed Water and Solid Poly(vinylpyrrolidione)" Pharmaceutical Research, vol. 10, No. 6, Jun. 1993, pp. 791-799.
U.S. Appl. No. 10/307,481, Notice of Allowance dated Mar. 30, 2006.
U.S. Appl. No. 10/856,782, Notice of Allowance dated Jul. 23, 2010.
U.S. Appl. No. 12/870,463, Notice of Allowance dated Mar. 21, 2013.
Liang, et al., "Self-Humidifying Membrane Electrode Assembly Prepared by Adding PVA As Hygroscopic Agent in Anode Catalyst Layer", International Journal of Hydrogen Energy 37, Jun. 27, 2012, pp. 12860-12867, Elsevier.
U.S. Appl. No. 12/819,273; Office Action dated Mar. 1, 2016.
European Patent Application No. 10014341.1, Office Action dated Nov. 30, 2016.
Lee et al., "Hydrophilic Polyurethane Coated Silver/Silver Chloride Electrode for the Determination of Chloride in Blood," Electroanalysis, Apr. 1999, vol. 11 (4), pp. 260-267.
Japanese Patent Application No. 513633/2007 Office Action dated May 19, 2009, including English Translation.
English Translation of Taiwanese Patent Application No. 92133910 Office Action dated Jun. 17, 2009.
European Patent Application No. 05749776.0, Office Action dated Jan. 7, 2014.
European Patent Application No. 05749838.8 Office Action dated Jun. 30, 2016.
European Search Report for Application No. EP10014341, mailed on Feb. 3, 2011, 7 Pages.
Indian Patent Application No. 8019/DELNP/2006, Hearing Notice dated Jul. 18, 2016.
International Preliminary Report on Patentability for Application No. PCT/CA2005/000842, mailed on Sep. 21, 2006, 13 pages.
International Preliminary Report on Patentability for Application No. PCT/CA2005/000843, mailed on Dec. 4, 2006, 7 pages.
International Search Report and Written Opinion for Application No. PCT/CA2005/000842, mailed on Sep. 9, 2005, 7 pages.
International Search Report and Written Opinion for Application No. PCT/CA2005/000843, mailed on Sep. 13, 2005, 10 pages.
International Search Report for Application No. PCT/CA2003/001841, mailed on Mar. 11, 2004, 4 pages.
Schacht, "Polymer Chemistry and hydrogel systems", Journal of Physics: Conference Series 3, Nov. 2004, pp. 22-28.
Supplementary European Search Report for Application No. EP05749776, mailed on Jun. 18, 2010, 3 Pages.
U.S. Appl. No. 10/856,929, Notice of Allowance dated Mar. 31, 2010.
U.S. Appl. No. 12/870,463, Office Action dated Nov. 7, 2012.
U.S. Appl. No. 13/923,845, Office Action dated May 4, 2016.
U.S. Appl. No. 10/856,929 Office Action dated Jun. 16, 2008.
Office Action mailed for U.S. Appl. No. 12/819,273, dated Oct. 18, 2016.
Canadian Patent Application No. 2869920, Office Action dated Feb. 23, 2017.
Brown et al., "Solute Diffusion in Hydrated Polymer Networks," Journal of the Chemical Society, Jan. 1975, vol. 71, pp. 12-21.
Mussini, "Concentrated "Equitransferent" Salt Bridges to Minimize Liquid Junction Potentials? A Revision," Journal of Chemical Education, Mar. 1988, vol. 65 (3), pp. 242-243.
Palin et al., "Determination of Diffusion Coefficients of Water in Cellulose Acetate Membranes," Journal of Applied Polymer Science, Apr. 1975, vol. 19, pp. 1135-1146.
U.S. Appl. No. 12/819,273, Non-Final Office Action dated Jul. 11, 2017.

\* cited by examiner

DIAGNOSTIC DEVICES INCORPORATING FLUIDICS AND METHODS OF MANUFACTURE

CROSS-REFERENCE TO RELATED APPLICATIONS

This application is a divisional application of U.S. patent application Ser. No. 12/870,463 filed Aug. 27, 2010, which is a continuation of U.S. patent application Ser. No. 10/856,782 filed Jun. 1, 2004 now U.S. Pat. No. 7,842,234 issued Nov. 30, 2010 and entitled Diagnostic Devices Incorporating Fluidics And Methods Of Manufacture, which is a continuation in part of U.S. patent application Ser. No. 10/307,481 filed Dec. 2, 2002 now U.S. Pat. No. 7,094,330 issued Aug. 22, 2006 and entitled Heterogeneous Membrane Electrodes, the contents of all of which are herein incorporated by reference.

FIELD OF THE INVENTION

This invention relates to unit-use diagnostic test cards comprising sensors and fluidics and to card readers therefor.

BACKGROUND OF THE INVENTION

Plastic cards in the general shape and size of credit cards, but with embedded integrated circuit chips are well known in the art. Such devices have appeared as articles of commerce in numerous applications where low cost electronic devices for personal use are required, such as bank cards, phone cards and the like. They are known as smart cards or IC cards. There was no teaching in the prior art concerning the use of card systems of this type that have been modified by removal of the integrated circuit chip and addition of fluidic and sensor elements for use in chemical analysis or in-vitro diagnostics, prior to the following published disclosures which are related to this invention: Electrode Module U.S. Pat. No. 6,896,778, and Point-of-Care In-Vitro Blood Analysis System U.S. Pat. No. 6,845,327.

In the patent entitled Heterogeneous Membrane Electrodes, U.S. Pat. No. 7,094,330, there is disclosed a diagnostic card containing a sensor array on an electrode module comprising a heterogeneous membrane reference electrode and electrochemical indicator electrodes, the disclosed electrode module being contained in a credit card sized fluidic housing. This present patent application now discloses additional inventive components and inventive elements of an electrode module and a diagnostic card incorporating fluidic elements.

Diagnostic test cards and cartridges for chemical analysis are well known in the art. Diagnostic cards and cartridges incorporating sensors and fluidic elements are known in the art. Early examples are U.S. Pat. No. 4,301,412 that discloses a pair of electrodes in a plastic housing with an orifice for sample introduction and a capillary conduit for sample flow to the electrodes. Similar devices were also disclosed in the capillary flow technology described in U.S. Pat. No. 5,141,868. Diagnostic card devices with sensors and fluidics also incorporating on-board fluids contained in sealed housings within the cartridge were disclosed in U.S. Pat. Nos. 4,436,610 and 4,654,127. The '127 device consisted of a plastic card-like housing with sensors and conduits with a sealed chamber containing a calibrating fluid mounted on the card. In use of this device the seal of the fluid-containing chamber was ruptured when the user manually turned a chamber element and subsequent fluid propulsion to the sensors on the card was by gravity. An improved diagnostic cartridge with sensors, fluid conduits and on-board fluid was disclosed in U.S. Pat. No. 5,096,669. This device consisted of a sensor array on a microfabricated silicon chip in a plastic housing with fluidic conduits, as well as a sealed pouch containing a calibrating fluid. The improvement was that the device was designed so that the fluid containing pouch could be ruptured and calibrating fluid moved to the sensors by the read-out instrument rather than manually. In the use of this device the sample is collected into the card away from the sensors, then subsequently moved to the sensor location by an instrument means. In both the '127 and '669 patents the fluid seal is made by a foil coated element and its rupture is by a piercing element that rips through the foil. U.S. Pat. No. 5,325,853 discloses a diagnostic device with sensors and fluidics with on-board fluid that is not sealed remotely from the sensors.

Of the devices of the prior art only the '669 device has proven commercially useful for the measurement of a broad range of analytes in parallel in sensor panels. The '669 device incorporates many unique and proprietary designs and special purpose components. The manufacturing processes also are unique to their devices and specialized assembly equipment is required. The '669 device and other prior art diagnostic devices generally require numerous process steps in electrode manufacture and numerous piece-parts and precision assembly steps in the card manufacture. Thus, this technology has proven expensive to manufacture, thereby limiting the broader utilization of the technology.

There are also performance limitations of the '669 technology. The fluid in the foil-lined and sealed reservoir has very limited shelf stability because the seal lengths are short. Furthermore, the reservoir is pressurized during fabrication and the sealed reservoir is ruptured during use by piercing the foil reservoir under applied pressure. Therefore the fluid in the reservoir is under pressure and, thus, has the potential to be evacuated from the reservoir in an explosive manner causing a potential for segmented fluid flow. Such problems can reduce the reliability of the '669 device. The sample transfer into the sample collection area of the '669 device is not done anaerobically. This may result in errors when measuring dissolved gases such as oxygen and carbon dioxide, particularly in samples which have low buffer capacity for those gases. Furthermore, there is no provision for reliable thermostating of the test fluid adjacent to the sensors.

There is now a need to provide for simpler and more generic designs and manufacturing procedures for sensor arrays and fluidics in diagnostic-card devices.

SUMMARY OF THE INVENTION

The current patent teaches designs and manufacturing processes to realize fluidic elements in diagnostic cards consisting of low cost components and manufacturing processes. This approach leads to significantly simpler devices than those of the prior art. There are fewer assembled parts, processes are generic and use generic equipment performing low tolerance assembly processes. The result is that devices according to this invention can be manufactured cost-effectively. Furthermore the diagnostic card of this patent incorporates many new inventive features which address performance limitations of prior art devices.

The invention provides a diagnostic card for use with a card reader in sensing at least one component concentration of a fluid sample. The diagnostic card includes a card body, at least one component sensor located in a sensor region in the card body, a sealed chamber defined in the card body for containing a fluid, preferably remote from the sensor region, a fluid conduit for fluidically connecting the chamber with the sensor region, a valve for fluidically connecting the chamber to the fluid conduit, and a delivery structure separate and distinct from the valve for forcing fluid from the chamber and into the fluid conduit, when the chamber contains fluid and is fluidically connected to the fluid conduit. In a preferred embodiment, the chamber is a hermetically sealed fluid reservoir, preferably in the form of an aluminum foil-lined cavity. The chamber is preferably filled without pressurization so that the contents of the sealed chamber are not under pressure when the chamber is connected to the fluid conduit by the valve. Furthermore, the valve preferably fluidically connects the chamber to the fluid conduit without simultaneous pressurization of the fluid in the chamber. The valve preferably includes a valve body for rupturing a chamber wall from within the chamber. The valve preferably includes a valve body displaceably received in a valve seat in the card body, the valve body being within the chamber, the valve body and valve seat being shaped and constructed for pinching and rupturing a wall of the chamber upon displacement of the valve body relative to the valve seat. The valve body is preferably a rupture plug and the valve seat is preferably a plug receiving bore in the card body, with the plug and plug receiving bore having cooperating edges for rupturing the chamber wall upon displacement of the plug in the plug receiving bore.

The invention further provides a sensor array on an electrode module incorporated into a credit-card sized plastic card body. The electrode module preferably includes a thin slab that is a laminate of an epoxy foil with a gold coated copper foil. The upper surface of the module is the epoxy foil which is perforated with holes. The lower surface of the module includes the gold coated copper foil which has been formed into an array of at least two electrodes. Each electrode of the array includes a formed element in the shape of a strip which constitutes an elongated electrical path connecting a contact end or contact pad at one end for connection to an external electrical circuit in a card reader, and a sensor end or sensor region under a hole through the epoxy at its other end. The module preferably comprises an array of such strip electrodes, each having a conductor path, a contact end and a sensor end, each sensor end of the array being located at a different hole in the epoxy foil. A sensor is formed on an electrode of the array when a sensor membrane or membranes are deposited into a hole in the epoxy on the top surface of the module, thus contacting the sensor region of the metal electrode on the bottom surface. In a preferred embodiment, a sensor array is made by depositing a different sensing membrane into each hole of each electrode sensing region of the electrode array.

The module is sealed to the plastic card body so that its upper epoxy surface including the sensor membranes face a fluidic conduit within the card body and the lower metalized surface faces outward and is exposed for external access to the contact pads. The array of holes with sensor membranes, referred to herein as the sensor region, is preferably a substantially linear region extending along the center of the module, which region aligns to a substantially linear fluidic conduit in the plastic card body so that fluid flowing through the fluidic conduit during use of the device contacts the sensor membranes of the array in the sensor region. The portion of the module's epoxy surface not located in the sensor region is sealed off by adhesive between the plastic card body and the module so that fluids are retained within the conduit at the sensor region and do not escape to or around the edge of the module.

In a preferred embodiment, the metal layer of the electrode module further includes a metal heater element in a heating region on its lower surface that is electrically isolated from the sensor electrodes and intended for contact with a first heater block contained in a card reader. The module's metal heater element is a formed element in the shape of a split ring which substantially surrounds the sensor region of the sensor array. The ring is split at one, two or more locations, that is to say the metal heater element preferably comprises of two or more shaped metal elements which together form the split ring surrounding the sensor region of the module. Each split represents a connecting gap connecting the sensing and contacting regions of the module. Each electrode of the electrode array now has the conductor path which connects the sensor end of the electrode to the contact end passing through a connecting gap so that the electrodes of the array are electrically isolated from the metal of the heater element. The conductor paths of the electrode array are preferably formed so that they are especially long and thin so that heat transport from the sensor region to the contact region is minimized. In one embodiment, a separate connecting gap is provided for each conductor path. In another preferred embodiment, the contact ends and connecting gaps are distributed about the sensing region so that all conductor paths are of equal length.

During use, a diagnostic card in accordance with the invention is inserted into the card orifice of a read-out instrument. The card's electrode module makes electrical contact at each of the contact pads of the electrode array to a z-action connector contained within the card reader. The card's electrode module also makes contact at its metal heater region to a first heater block also contained within the card reader. The first heater block is coplanar with the card's module surface and proximal to it when the card is in the card-reader's card insertion orifice. The first heater block makes physical contact to the metal heater region of the module, but also extends to cover the entire sensor region and a substantial region of the electrical paths, in close proximity but not in physical contact. This allows efficient heat transfer to the paths, but maintains electrical isolation from them. Thus, the first heater block heats the sensing region of the module and the fluid in the card's fluidic conduit above the sensing region by direct thermal conduction from the block to the module's metal heater region, as well as indirectly through an air gap at the sensor region and thence to the sensors and fluids, and indirectly through a thin air gap to the electrical paths of the electrode array. This configuration accomplishes thermal bootstrapping of the electrode paths, which further minimizes the heat transport from the sensor region to ambient along the paths. This configuration thus provides for more uniform temperature control of the sensor region. A second heater block of the card reader is coplanar with the card's upper surface and proximal to it when the card is in the card-reader's card insertion orifice. The second heater block makes physical contact to the card's upper plastic surface. The second heater block covers the sensor area of the card but extends a distance along the direction of the fluidic channel in both directions away from the sensor area. This provides heat to the fluid in the fluidic conduit in the regions immediately upstream of the sensor area and immediately downstream. This minimizes heat flow from the sensor region along the fluidic conduit by effectively thermally bootstrapping the fluid in the conduit. Thus the card's entire sensor area, the fluidic conduit proximal to the sensor area, the sensors' electrical paths and the fluid in the conduit upstream and downstream of the sensor area are all contained within a thermostatted cavity comprising heater blocks above and below. This arrangement allows rapid heating of a cold sample fluid to its control temperature, and also accomplishes very precise thermostatting to the control temperature.

In another aspect of the diagnostic card of this invention there is provided a connector means in the read-out device for connection to the card's electrode module. The connector means is a z-action connector comprising an array of contact elements, being formed metal films on a flex substrate, which flex-substrate is placed on a flexible cantilever, preferably a plastic cantilever. The cantilever is positioned so that when the card is inserted into the card reader's card insertion orifice the module's outer surface with its contact pad array is proximal to the contact elements of the flex substrate and the cantilever is depressed so as to apply z-action force between the connector array on the flex substrate and the contact pad array on the module. Because the electrical contacting elements are thin metal films on a flex substrate, the invented flex connector drains far less heat than conventional z-action connector pins used to contact smart cards of the known art. Additionally, the flex substrate and its connector array can also incorporate electronic components of card reader's electrical circuitry, resulting in a cost reduction of the card reader.

In still another aspect of the diagnostic card of the invention there is provided an improved design for the sealed calibrator reservoir. In the previously disclosed card of U.S. Pat. No. 7,094,330, the calibrator reservoir comprised a cavity in the card's plastic body, which after filling with calibrator fluid was sealed by an overlayer of a metal coated foil element. We have found improved lifetime of the sealed calibrator when the cavity in the plastic card body is clad on both sides with an aluminum foil lamination. The new design comprises a diagnostic card with a sensor array on an electrode module, and a sealed calibrator fluid reservoir, which when the seal is ruptured during the use of the device, becomes fluidically connected to the module's sensor region. The reservoir comprises a cavity in the card body, a first plastic-film-coated aluminum foil deformed into the cavity so that the foil contacts the plastic surface of the cavity with its aluminum surface facing the plastic of the cavity and the foil extends beyond the perimeter of the cavity, a calibrator fluid in the cavity, and a second plastic-coated aluminum foil element overlaying the first with its plastic surface facing the plastic surface of the first foil element, and a fused plastic-to-plastic seal between the two foil elements which hermetically seals the calibrator fluid, the seal being formed in the region around the perimeter of the cavity. For good room temperature stability of the calibrator fluid in the sealed reservoir, we have preferred that the width of the perimeter seal be at least 3 mm along the entire perimeter, thus providing a long leakage path for material to escape through the fused plastic seam joining the first and second metallized cladding layers.

In another aspect of the improved calibrator fluid reservoir, there is provided an improved rupture means for automatically rupturing the foil seal upon use of the device, so as to enable the subsequent delivery of calibrator fluid to the measurement cell which is the fluidic cavity above the sensor region of the card's electrode module. In this improved rupture means there is a plug sealed between the metal foil cladding elements of the calibrator chamber. This plug is caused to move when the card is inserted into the card reader's card insertion orifice which movement causes rupture of the metal foil cladding. A conduit fluidically connects the calibrator reservoir at its point of rupture to the measurement cell, enabling displacement of calibrator fluid to the measurement cell after rupture of the seal.

In another aspect of the diagnostic card of the invention there is provided an improved design for the sample entry port. An adhesive gasket around the sample entry hole in the card's housing permits a reliable fluid-tight seal between a syringe containing sample fluid and the card. A reliable seal results with little skill required by the operator to engage the syringe to the card.

All inventive aspects of the diagnostic card of the invention are preferably accomplished in a substantially flat credit-card sized form. Being flat enables efficient stacking of the cards during their storage, as well as enabling a simple engagement to two coplanar clamping elements in the card reader's card insertion orifice.

BRIEF DESCRIPTION OF THE DRAWINGS

Preferred embodiments of the invention will now be described in more detail by way of example only and with reference to the attached drawings, wherein.

DETAILED DESCRIPTION OF THE PREFERRED EMBODIMENTS

We describe herein in more detail a preferred embodiment of a diagnostic card in accordance with the invention, formatted for use with a sensor array on an electrode module.

Figure 1A:
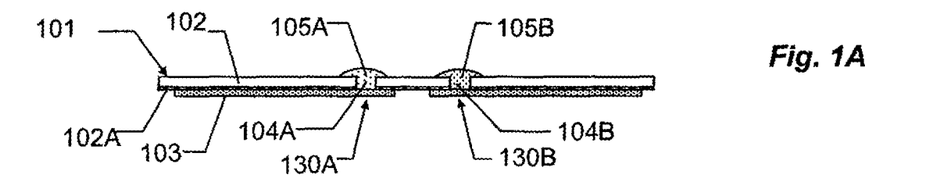
FIG. 1A is a side view schematic of one preferred embodiment of an electrode module and sensor membranes in accordance with the invention.

FIG. 1A shows a cross-sectional view of an electrode module, fabricated using standard smart-card chip-module technology known in the art. The electrode module is described in detail in U.S. Pat. Publ. No. US 2002/017944 A1, which is incorporated herein by reference. We now disclose new inventive features of the module and its use as part of the diagnostic card and card reader.

The module 101 of FIG. 1A comprises an epoxy foil element 102 laminated to a gold coated copper metal foil 103 with optional adhesive 102A. The epoxy foil element 102 has through-going holes at 104A and 104B. The metal foil 103 is formed into an array of electrode elements 130. The construction of the electrode elements will be discussed in the following by way of a pair of electrode elements 130A and 130B. Each electrode element 130A and 130B has a connection end 131A, 131B for connection to a measuring circuit in a card reader (not shown) and a sensor end 132A and 132B under the through-going holes in the epoxy 104A and 104B. The electrode module is received from the vendor on a 35 mm web. During manufacture, membranes 105A and 105B are applied to the module on the web extending laterally beyond the perimeter of the holes 104A, 104B and overlaying the top epoxy surface, and extending through the holes to contact the metal electrodes at the sensor ends 132A and 132B. After printing of the membranes, the module is excised from the web using a die cutter, then placed and sealed into a housing in the diagnostic card as described later. In the preferred embodiment, the excised module of the FIG. 1 design is about 11 mm square by 120 micrometers thickness.

Figure 1B:
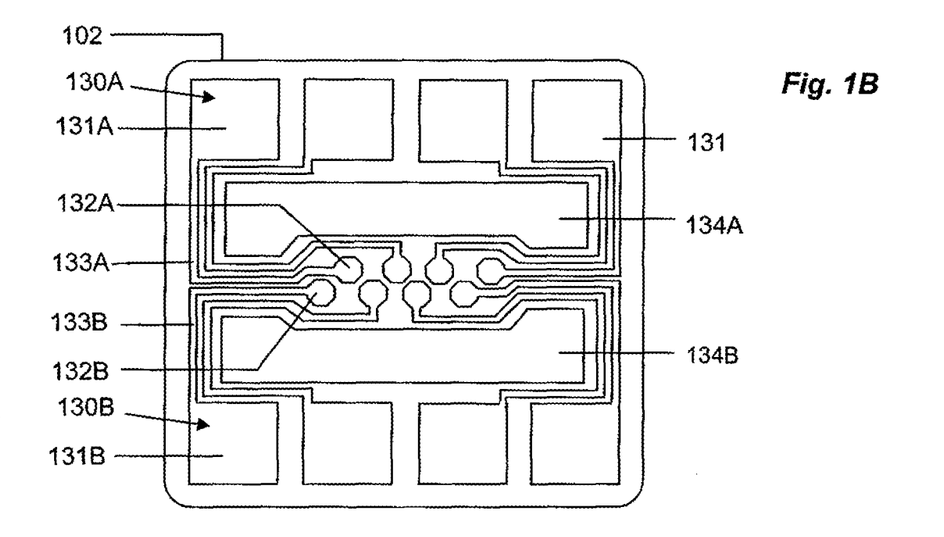
FIG. 1B is a bottom view schematic of another preferred embodiment of an electrode module in accordance with the invention and showing the positioning of the metal foil elements.

FIG. 1B shows a bottom view (metal foil side) of a module with eight electrode elements, comprising the laminated epoxy foil 102 and metal foil 103. This figure shows in more detail the spatial arrangement of the metal electrode elements. As in FIG. 1A, two electrodes 130A, 130B, representative of the eight, are labeled to show the relationship between their sensor ends 132A and 132B and their connection ends 131A and 131B. There is a metal conductor path 133A, 133B between each electrode's sensor end 132 and its connection end 131, the path 133A extending between connector end 131A and sensor end 132A and the conductor path 133B extending between the connector end 131B and sensor end 132B. The metal conductor paths 133 are generally long and thin to minimize lateral heat transport along them when the module is being heated. Heater contacts 134A, 134B of the metal foil 103 are electrically isolated from the eight electrode elements. These regions are for physical contacting by a heater block of the card reader, as described in more detail later.

Figure 1C:
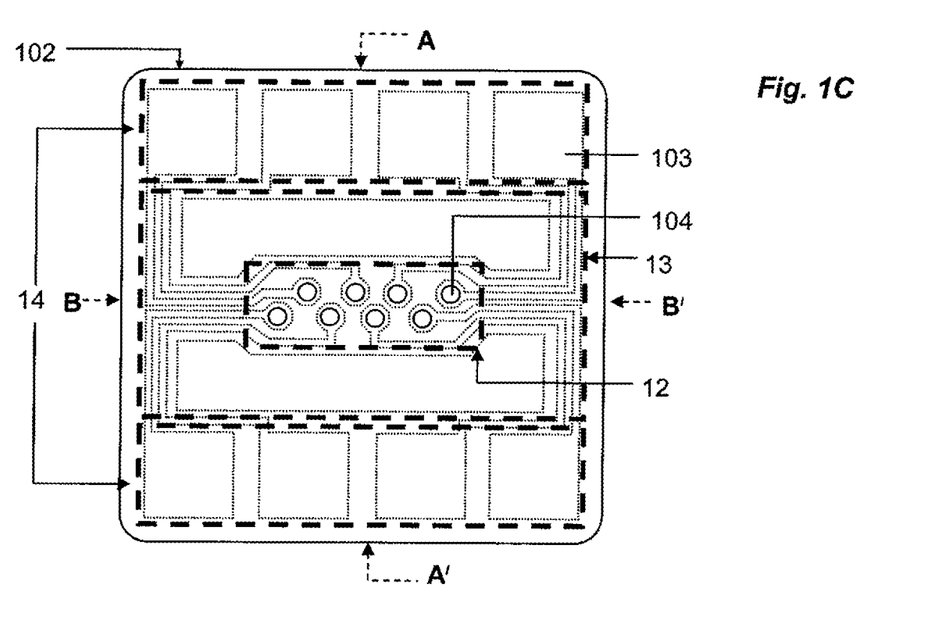
FIG. 1C is a top view schematic of an electrode module showing the sensor region, the heater region and the contact region of the embodiment of FIG. 1B.

FIG. 1C shows the module of FIG. 1B in top view (epoxy foil side). The position of the electrodes on the underside of the module is shown in the narrow dashed line. The electrodes are not labeled for reasons of clarity. Also shown is the position of the through-going holes 104 in the epoxy relative to the underside metal electrodes. As shown diagrammatically, the layout of the module comprises three distinct regions. The central region of the module is the sensor region 12. This region of the module is proximal to a fluidic conduit in the card when the module is assembled into the diagnostic card, as described later. The region proximal to the location of the lower heater block of the card reader when the card is in the card reader's card insertion orifice is the heater contact region 13. More details of the relationship of the heater blocks of the card reader to the module in the card are given later. The region on the periphery of the module where electrical contact is made by the card reader to the metal electrodes on the underside of the module is the contact region 14. Those skilled in the art will appreciate that the same standard module fabrication technology can be used to make modules with many different electrode numbers and geometries. They differ only in the tooling to provide different locations of the through-going holes 104 (see FIGS. 1A and 1B), and the mask art-work used to photolithographically define different spatial arrangements of the formed metal elements 103. The general arrangement of any module according to this invention will include a sensor region 12 approximately centrally located, a heater contact region 13 at least partially adjacent the sensor region, and an electrical contact region 14 toward the module's periphery.

Figure 2A:
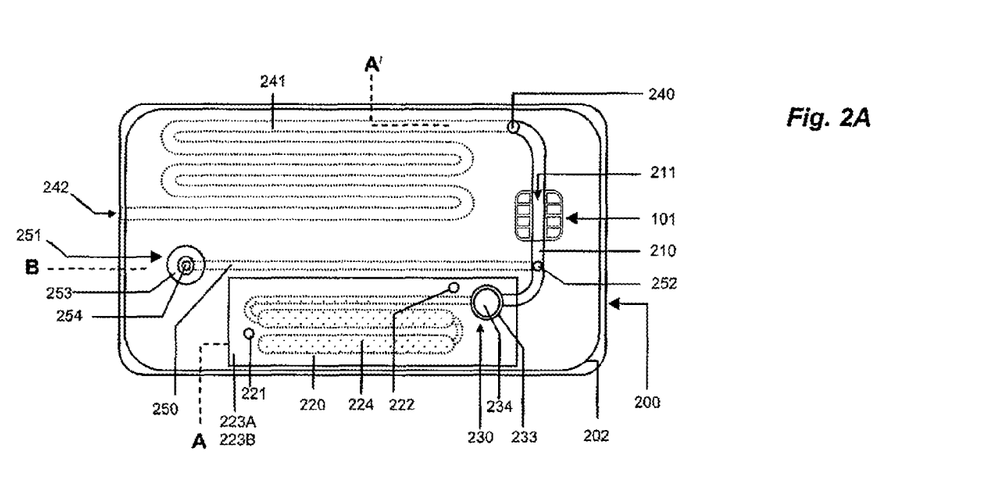
FIG. 2A is a top view schematic of one preferred embodiment of a diagnostic card in accordance with the invention including an electrode module and a sealed calibrator fluid chamber with fluidic connections.
Figure 2B:
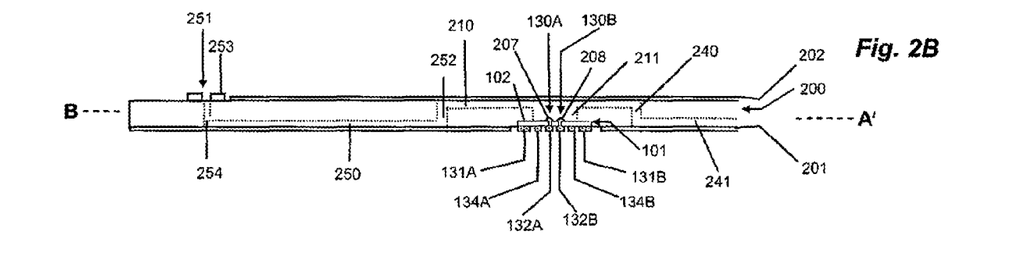
FIG. 2B is a side view schematic of the embodiment of FIG. 2A shown in cross-section taken along the fluidic path BA' shown in FIG. 2A.
Figure 2C:
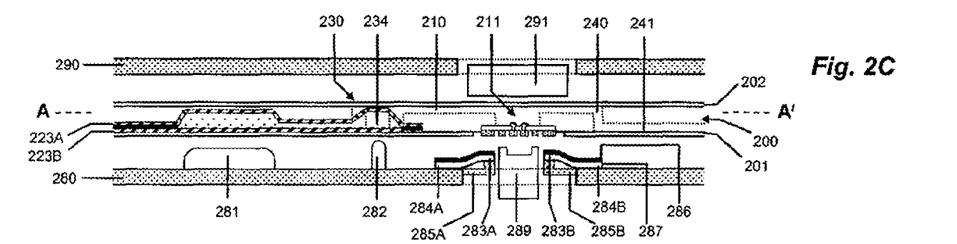
FIG. 2C is a side view schematic of the embodiment of FIG. 2A shown in cross-section taken along the fluidic path AA' shown in FIG. 2A, and the card insertion orifice of the card reader.
Figure 2D:
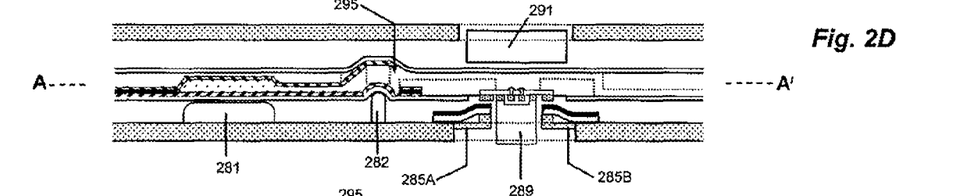
FIG. 2D is a side view schematic of the embodiment of FIG. 2A shown in cross-section taken along the fluidic path AA' shown in FIG. 2A, and the partially clamped card insertion orifice of the card reader.
Figure 2E:
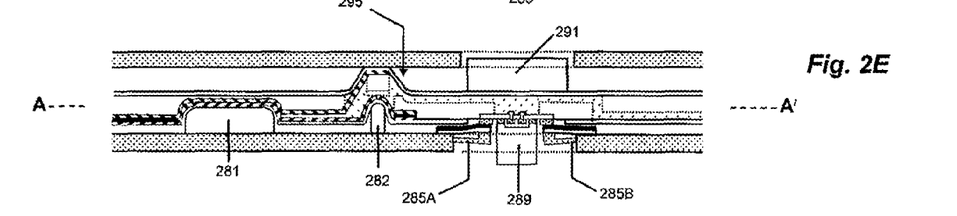
FIG. 2E is a side view schematic of the embodiment of FIG. 2A shown in cross-section taken along the fluidic path AA' shown in FIG. 2A, and the fully clamped card insertion orifice of the card reader.

FIG. 2A shows a top plan view and FIGS. 2B-E show cross-sectional schematic views of a preferred embodiment of a diagnostic card in accordance with the invention, including a sensor array on an electrode module, including the card's relationship to elements of the card reader's card insertion orifice when the card is in the card insertion orifice during the use of the card. FIG. 2B shows one cross-sectional schematic taken along the fluidic path AA' of FIG. 2A, the fluidic path extending from a calibrator fluid chamber 220 along a fluidic channel 210, through the measurement cell 211 to a waste channel 241. FIGS. 2C-E show schematics along the fluidic path BA' of FIG. 2A, being along a fluidic path from the sample entry port 251 through the measurement cell 211 to the waste channel 241.

Referring to FIGS. 2A and 2B, the diagnostic card in the preferred embodiment is formed from a credit-card sized (85 mm×53 mm×1 mm thick) molded plastic card body 200 with an electrode module 101 as generally described above with reference to FIGS. 1A-1C embedded in the lower surface of the card body. The electrode module comprises an epoxy foil element 102 with die-cut through-going passages, the epoxy element being laminated with a metal foil that has been formed into eight electrode elements. Two electrode elements 130A, 130B are shown in FIG. 2B which have a sensor end 132A and 132B respectively and a contact end 131A, 131B respectively as are shown in the side-view schematic diagram. Membranes 207 and 208 are shown on the top surface of the module and contacting underside metal elements at the sensor ends 132A and 132B through the passages in the epoxy. The card body 200 also contains molded features (grooves, trenches and holes) on both its upper (solid lines in the top view schematic) and lower (dotted lines in the top view schematic) surfaces which molded features, when sealed by other laminating elements, form fluidic channels and a sealed fluid reservoir. Laminations are made to the lower and upper surface of the housing by label elements 201 and 202 and by metal foil elements 223A and 223B. Elements 201, 202 on the lower and upper surfaces of the card are label elements die-cut from an adhesive coated polymer sheet. Elements 223A and 223B are a lamination of two elements which are die-cut from a sheet of metal foil coated with polyethylene for heat sealing.

Figure 4A:
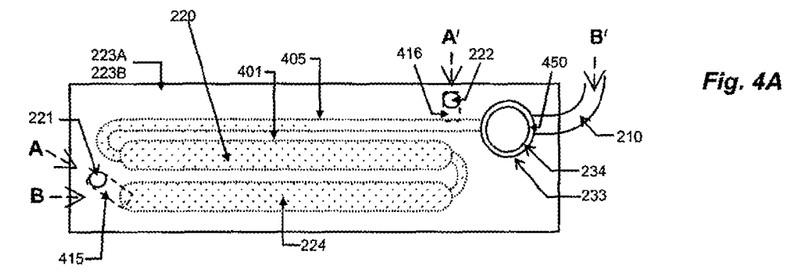
FIG. 4A is a top view schematic of the calibrator fluid chamber and valve of the card embodiment of FIG. 2A.
Figure 4B:
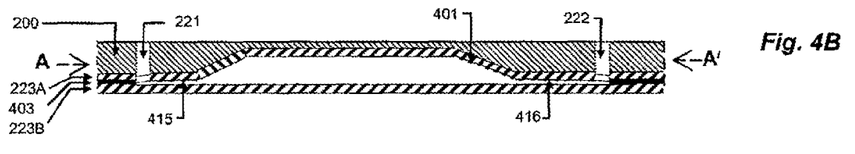
FIG. 4B is a side view schematic of the calibrator fluid chamber (before fluid fill) of the card embodiment of FIG. 2A shown in cross-section taken along AA' shown in FIG. 4A.
Figure 4C:
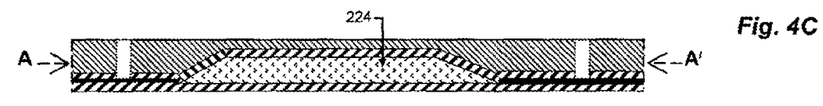
FIG. 4C is a side view schematic of the calibrator fluid chamber (after fluid fill and seal) of the card embodiment of FIG. 2A shown in cross-section taken along AA' shown in FIG. 4A.
Figure 4D:
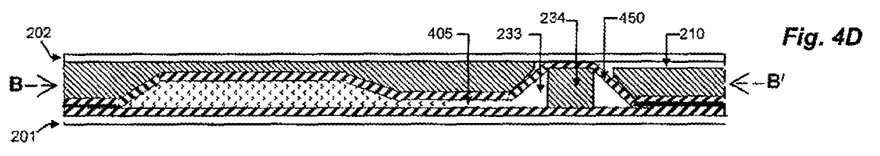
FIG. 4D is a side view schematic of the calibrator fluid chamber (after fluid fill and seal) of the card embodiment of FIG. 2A shown in cross-section taken along BB' shown in FIG. 4A.

There are two trenches side by side on the lower surface of the plastic body. When clad by laminating elements 223A and 223B they form a reservoir chamber 220 with a volume of about 150 microliters. There is an orifice 221A through the plastic body 200 through which a calibrator fluid 224 is injected from the upper surface of the body to fill the chamber 220 during card manufacture, with another orifice 222, also through the body 200, for venting of air during the filling process. The chamber walls are defined by a pair of opposite foil elements 223A and 223B made of a plastic coated meal foil. The chamber 220, after filling with fluid, is completely sealed when the orifices 221 and 222 are closed-off during the lamination of foil elements 223A and 223B as is described in more detail later with reference to FIGS. 4B-D.

There is a fluidic channel 210 connecting the calibrator fluid chamber 220 to the measurement cell 211 at the electrode module's sensor region, and then to a waste channel 241. The diagnostic card also includes a sample inlet port 251 which is in fluid communication with a second channel 250 connecting the sample inlet port 251 to the measurement cell 211. There is a chamber outlet valve 230 for fluidically connecting the calibrator fluid chamber 220 with the connecting channel 210 between the measurement cell 211 and the calibrator fluid chamber without pressurizing fluid contained within the chamber. This means the valve structure is operated/operable independent of any pressurization of fluid in the chamber. The valve is preferably a rupturing structure for rupturing the wall of the sealed chamber at the connection with the connecting conduit for fluidically connecting the chamber to the conduit. In this preferred embodiment, the chamber rupturing structure includes a bore 233 through the body 200 and a rupture element, in this case plug 234, located in the bore and within the chamber 220 between the two metal foil elements 223A and 223B. The plug is slightly smaller in diameter than the bore, rendering it capable of axial movement therein, in this case upwards. The plug 234 is positioned so that a region of the metal foil element 223A on the peripheral edge of the plug (295 of FIG. 2D) ruptures when the plug is pushed upwards. Any other structures useful for the controlled opening of the chamber 200 for connection with the channel 210 when the card is in the card reader can also be used to function as the valve 230, as long as they do not lead to a pressurization of the chamber 220 during opening of the chamber. The diagnostic card further includes a delivery structure for forcing fluid from the chamber 220 under pressure, when the chamber contains fluid, and into the connecting conduit 210. In the preferred embodiment, the delivery structure is a portion of the chamber walls which is sufficiently flexible to be deformed, preferably from the exterior of the card and while the card is inserted in the card reader. Of course, the delivery structure can also be any other structure usable for reliably forcing fluid from the chamber when the chamber is fluidically connected to the connecting conduit.

FIGS. 2C-E schematically show the card in the card orifice of a card reader (the card reader preferably including a circuit board with detectors, amplifiers and other circuit components, as described in U.S. Pat. No. 6,845,327 and illustrate the spatial relationship between elements of the card and elements of the card-reader's orifice during use of the device. In use, the card is first inserted into a card reader's card insertion orifice (FIG. 2C). The orifice comprises a lower generally planar mating element 280 which is co-planar with and proximal to the card's lower surface, and an upper generally planar mating element 290 which is co-planar with and proximal to the card's upper surface.

The card reader's card insertion orifice has a guide (not shown) to locate the features on the card with their respective mating features on the card reader insertion orifice's planar mating elements during card insertion. After insertion, the two mating elements of the card reader insertion orifice are moved toward each other, thus clamping the card between them. The construction and function of the card reader is described in detail in U.S. Pat. No. 6,845,327, incorporated herein by reference. As the lower surface of the card is brought into contact with the lower mating element 280 of the card reader's card orifice, a pin element 282 provided on the mating element 280 first contacts the card at the calibrator fluid chamber outlet valve 230. The pin 282 pushes plug 234 upwards. This lifts the metal foil laminate above the plug causing foil 223A to break at location 295 (FIG. 2D), thus fluidically opening the calibrator fluid chamber. At the same time, the electrode module is electrically contacted by a contacting means of the card reader which comprises a contacting array of eight metal contact elements formed in a metal film or foil 286 on an insulating flex connector substrate 287. Two of the eight pins are shown in the side view schematics of FIG. 2C-E. Each has a contact end 283A, 283B for making z-action contact to the module's electrode contact locations 131A, 131B on the lower surface of the electrode module, and an end 284A, 284B for connection to an electrical circuit elsewhere in the card reader. The flex connector at its module contacting end is mounted on the movable end of a set of flexible cantilevers 285A and 285B, preferably made of plastic, whose other end is embedded in the lower mating element 280 of the card reader orifice The cantilevers, with the flex connector mounted on it, are in their at-rest position raised above the plane of the lower mating element 280 at the location of contact to the module, so that as the card is clamped to the lower mating element of the card reader orifice the cantilevers are depressed, thus providing z-action contact force to the electrical contacts made between the flex connector of the card reader and the electrode module of the card. At the same time the card's electrode module is thermally contacted by a lower heater block 289 and the top of the diagnostic card above the measurement chamber by an upper heater block 291. The lower heater block 289, which is mounted in the card reader orifice's lower mating element 280, makes thermal contact with the module on its lower surface directly under the measurement chamber 211, making physical contact to the module's 'split ring' heater contact metal elements 134A, 134B, while being in close proximity to the other metal elements elsewhere on the module, but electrically isolated from them. At the same time, the upper heater block 291, which is mounted in the card reader orifice's upper mating element, makes thermal contact to the card directly above the measurement chamber 211. Each heater block contains a heater element and a temperature measuring element each in intimate thermal contact with the block (not shown). The blocks' heater elements and temperature measuring elements are also connected to the card reader's electrical circuit. The lower mating element 280 of the card reader also includes an actuator element 281 positioned to be opposite the calibrator fluid chamber 220 when the card is inserted into the card reader's card orifice. As the card continues to be clamped between the mating surfaces, the actuator element 281 now engages the delivery structure of the calibrator fluid chamber 220, deforming the chamber wall 223 and compressing the chamber 220, thereby pressurizing the chamber contents and causing delivery of fluid out of the chamber along fluidic channel 210 to measurement chamber 211 (FIG. 2E). When the card is fully clamped in the card reader orifice (FIG. 2E) there is a period of time during which the module, the sensors and the fluid in the measurement cell are heated, preferably to 37.4° C., followed by a period of time during which the module's sensors are calibrated. After this calibration period, the card-reader prompts the user to supply sample fluid to the diagnostic card. The user engages a syringe containing sample fluid to the card's sample entry port (251 of FIGS. 2A and 2B). The syringe tip forms a seal with an adhesive element 253 surrounding the entry port. The sample port 251 may optionally be reversibly sealed with a closure flap which can be part of the label 202. The user delivers sample fluid from the syringe to the measurement cell 211 along channel 250, thus displacing calibrator fluid out of chamber 211 to waste channel 241. The module's sensors now generate sensor signals derived from the sample fluid, which electrical signals are extracted from the electrode module via the card reader's electrical flex connector 287 to an electrical circuit in the reader. After completion of the measurement cycle, the card is unclamped and withdrawn from the card reader's orifice.

Referring again to FIG. 2, the card is assembled as follows in three principle steps. Step 1: sealing the electrode module 100 to plastic card body 200. Step 2: forming the metal foil cladding around chamber 220 by laminating first lamination 223A and second 223B lamination of metal foil elements with insertion of the rupture plug 234 between these laminations; filling of the clad calibrator chamber 220 with calibrator fluid 224; then sealing calibrator fluid and plug into the clad chamber. Step 3: laminate top 202 and bottom 201 labels. Steps 1 and 2 will now be described in more detail.

Figure 3A:
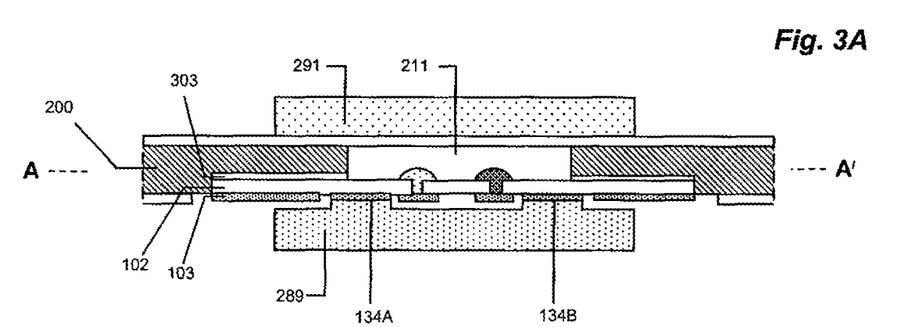
FIG. 3A is a side view schematic of the electrode module embodiment of FIG. 2A embedded in the body of the card of FIG. 2A shown in cross-section taken along line AA' of the electrode module of FIG. 1C, and the position of the card reader's heater blocks.
Figure 3B:
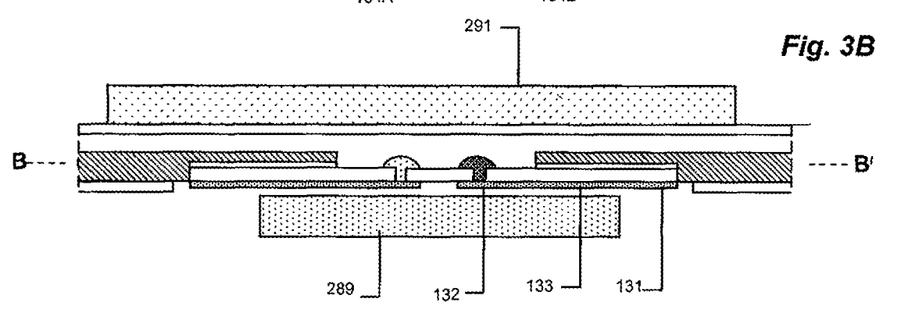
FIG. 3B is a side view schematic of the electrode module embodiment of FIG. 2A embedded in the body of the card of FIG. 2A shown in cross-section taken along BB' of the electrode module of FIG. 1C, and the position of the card reader's heater blocks.

FIGS. 3A and B show in more detail the electrode module assembled into the plastic card body 200 in step 1 of the assembly process. Referring to FIG. 3A, the molded plastic card body 200, as received from the vendor, is first laminated with the electrode module 100 whose epoxy foil upper surface 102 faces the card body and is recessed into it and sealed with adhesive 303. The adhesive is applied to the outer area of the module's epoxy surface perimetric to the module's central sensor region. As shown in FIGS. 3A and 3B the adhesive is applied to the entire top epoxy surface, except the sensor region (region 12 shown in FIG. 1C). The module, when embedded in the card, is coplanar with the card body with the module's upper sensor surface proximal to the card body's fluid measurement cell 211 and the module's lower metal surface 103 facing the outside.

FIGS. 3A and 3B also show in more detail the location of the card reader's heater blocks relative to the card and its electrode module when the card is clamped in the card reader's card insertion orifice. FIG. 3A shows a cross-section along AA' of the electrode module shown in FIG. 1C, which is in the direction orthogonal to the card's fluidic channel over the electrode module. FIG. 3B shows a cross-section along BB' of the electrode module shown in FIG. 1C, which is in the direction along the path of the card's fluidic channel over the electrode module. As shown in FIG. 3A, the lower heater block 289 physically contacts the electrode module at the locations 134A and 134B which are the electrode module's heater contact metal elements. The lower heater block 289 is in close proximity to (thus thermally connected with) but electrically isolated from, other metal elements of the electrode module 100, including the sensor ends 132 and contact ends 131 of the electrodes and the metal paths 133 between them. The lower heater block 289 extends a distance beyond the width of the fluidic measurement chamber 211. As shown in FIG. 3B the lower heater block is in close proximity to the metal paths 133 connecting the electrodes' sensor ends 132 to their contact ends 131 but not in physical contact with them. The upper heater block 291 makes contact to the card's upper plastic label. It too extends beyond the width of the measurement chamber 211 (FIG. 3A), but also extends a distance along the fluidic channel beyond the electrode module on both sides (FIG. 3B). We have found that when the upper heater extends about 5 mm beyond the module there is satisfactory thermal bootstrapping of the fluid beyond the sensor region of the module, thus assuring excellent thermal control of the temperature of the sensor region.

We have found that when the card is fully clamped in the card reader's orifice, at which time the lower heater block 289 contacts the electrode module's heater contacts 134, the regions of the heater block not in contact with, but in proximity to the module, should be spaced about 25 micrometers from the module's metal surface. At this distance there is still satisfactory heat transfer from heater block to module, but there is also reliable electrical isolation during repeated use of the card reader. In general, the rate of heat transfer from the heater block to the module increases with decreasing spacing. The preferred range of spacing is 10 to 50 micrometers. However, the person skilled in the art will appreciate that a spacing below 10 micrometers may be usable as long as reliable electrical insulation of the heater block from the sensing and contacting regions of the module is ensured. A spacing above 50 micrometers is usable, but the heat transfer rate will be low.

FIG. 4 shows in more detail the metal foil clad calibrator fluid chamber 220 and the foil rupturing plug, and its forming, filling and sealing processes which together are step 2 of the card assembly procedure. Referring to FIG. 4A which is a top view schematic of the card's calibrator fluid reservoir region and FIG. 4B which is a cross-section through the embodiment of FIG. 4A taken along line AA', being along the fluidic path from the calibrator fluid fill hole 221 along the calibrator fluid reservoir 220, its connecting channel 405 to the vent hole 222. The card body 200 in the calibrator fluid reservoir region of the card features a molded calibrator fluid reservoir cavity 401 (shown here as two parallel cavities fluidically connected), a molded trench 405 connecting the cavity 401 to a rupture-plug bore 233 and a second trench 210 connecting the rupture-plug bore to the measurement cell 211 (see FIG. 2A). A first metal foil element 223A has a pressure sensitive adhesive on one side of the metal and approximately 25 micrometers thickness polyethylene coating on the other. The element 223A, which is die cut from a sheet and placed with its adhesive side down onto the card body, extends over the calibrator fluid reservoir cavity 401, the connecting channel 405 and the rupture-plug bore 233, overlaying all these features and extending to a perimeter beyond them. When high air pressure is applied to the foil element 223A it deforms taking the contour of the card body's reservoir cavity 401, connecting channel 405 and rupture-plug hole 233, being then attached to the body's surface by the pressure sensitive adhesive. The polyethylene coated surface of foil element 223A faces the inside of the reservoir cavity. The foil deforming procedure is similar to the blow-molding process well known in the art. In manufacture, a tool with an air pressurizable cavity is engaged to the foil on the card body and sealed to it about the cavity, preferably by an elastomeric gasket. When high pressure air is introduced into the tool's cavity, the air blow-deforms the metal foil to take the contour of the card body. It will be readily apparent to the person skilled in the art that other methods of shaping the foil element 223A to take on the contour of the card body may also be used, such as hydroforming. A rupture-plug element 234, which is a rigid disc approximately the same thickness as the card body with a diameter somewhat smaller than the diameter of the rupture-plug bore 233, is placed onto the foil element 223A in the depression in the foil formed over the rupture-plug bore 233. The foil element 223A is pierced at the bottom of fluid fill hole 221 and vent hole 222. A second polyethylene coated metal foil element 223B is laminated over the first foil element 223A with its polyethylene coating facing the polyethylene coating of element 223A. A heat seal is made between foil elements 223A and 223B, by fusing the two polyethylene coating layers, everywhere except in the fill and vent regions 415 and 416 adjacent the fluid fill and vent holes 221 and 222 respectively. At this stage, the foil clad calibrator fluid reservoir is sealed except for the fill and vent holes 221, 222 as shown in FIG. 4B and is now ready to receive fluid. Calibrator fluid 224 is introduced through fill hole 221 into chamber 220 filling it and partially filling the channel 405 while expelling air from the chamber through vent hole 222. In the final step, once the chamber 220 is filled, the fill and vent regions 415 and 416 near the fill and vent holes 221, 222 are then sealed in a secondary heat seal process, thus entirely sealing the calibrator fluid and rupture plug within the two foil elements as shown in FIGS. 4C and 4D. Lamination of the card body 200 with an upper pressure sensitive adhesive coated label element 202 now forms a channel 210 which fluidically connects the region 450 of the calibrator chamber where the rupture of the foil takes place (FIG. 4D) with the measurement cell 211 (see FIG. 2A). A second lower label lamination 201, which leaves the lower surface of the electrode module 100 exposed, completes the card assembly.

Using the above recited fluid chamber design and manufacturing procedure we have achieved a remarkably long period of calibrator fluid storage stability. The mean time to failure of a sealed fluid used for sensor calibration is the time for the carbon dioxide partial pressure to drop from its initial value in the fluid to an unacceptably low level as the gas permeates out through the heat fused polyethylene seam. We have found that we can achieve greater than 6 months room temperature storage stability in which time the partial pressure of carbon dioxide changes from its average value by less than 0.5 mm Hg. To achieve this we have designed the perimeter seal width to be greater than 3 mm width at all locations along the perimeter. This high level of stability is in marked contrast to other devices of the known art, which must be stored in the refrigerator to achieve extended lifetime. Using the above recited fluid chamber design with incorporated rupture plug we have achieved a simple foil rupturing method which opens the foil-sealed chamber during the use of the device, but before the calibrator fluid in the chamber is pressurized to expel it from the chamber and to the measurement cell. This achieves a high level of reliability and control in the calibrator fluid delivery step of the device's operation.

Those skilled in the art will recognize that the various inventive elements of the diagnostic card can be used together as they are in the card of this disclosure, or they can be used separately in different card designs. For example, the sealed fluid chamber and its valve structure means can be incorporated into diagnostic cards comprising micro-porous fluidic elements such as those as disclosed in U.S. Pat. No. 7,722,817. In this case the sealed fluid is used for priming the micro-porous pump elements rather than for sensor calibration purposes. The inventive fluidic arrangements and sealed fluid chamber can be advantageously used with electrode modules comprising foil laminates as described in this disclosure, but they can also be used with sensor modules of other kinds, including the many types of sensor modules of the known art which are fabricated on a planar insulating substrates (microfabricated chips, planar circuit boards and the like) and including sensor modules incorporating non-electrochemical sensing means such as optical, chemiluminescence or fluorescence, as are known in the art. Indeed, these inventive fluidic components will be useful in any unit-use diagnostic card incorporating an on-board fluid.

The above-described embodiments of the present invention are intended to be examples only. Alterations, modifications and variations may be effected to the particular embodiments by those of skill in the art without departing from the scope of the invention, which is defined solely by the claims appended hereto.

What is claimed is:

1. A diagnostic card for use with a card reader in sensing at least one component concentration of a fluid sample, comprising:
   a card body
   at least one component sensor located in a sensor region of the card body;
   a sealed chamber defined in the card body outside the sensor region for containing a fluid, the chamber having a chamber wall sealing the chamber;
   a fluid conduit for fluidically connecting the chamber with the sensor region, when the chamber is opened;
   a valve for fluidically connecting the chamber to the fluid conduit, the valve having a structure for rupturing the chamber wall of the sealed chamber at the connection to the fluid conduit without pressurization of the chamber, thereby opening the chamber; and
   a delivery structure for forcing fluid from the chamber and into the fluid conduit, when the chamber contains fluid, the delivery structure being operable independently of the valve and being formed by a flexible portion of the chamber wall which flexible portion is deformable for reduction of the chamber by external application of a deforming force.

2. The diagnostic card of claim 1, wherein the chamber is formed of a laminate of two opposed, plastic coated metal foil laminations bonded about their perimeter by a first heat seal made by melt bonding the plastic coatings of the laminations.

3. The diagnostic card of claim 2, wherein the heat seal has a width of at least 3 mm.

4. The diagnostic card of claim 2, wherein the card body includes molded contours and one of the foil laminations is pressure-formed into the contours of the card body.

5. The diagnostic card of claim 2, wherein the card body includes molded contours and one of the foil laminations is pressure-formed into the contours of the card body.

6. The diagnostic card of claim 1, wherein the card body includes a valve seat and the valve includes a valve body displaceably received in the valve seat, the valve rupturing the portion of the chamber wall upon displacement of the valve body relative to the valve seat.

7. The diagnostic card of claim 1, wherein the chamber has a chamber volume and the flexible portion of the chamber wall is deformable for reduction of the chamber volume.

8. The diagnostic card of claim 1, wherein the chamber has a chamber volume and the flexible portion of the chamber wall is deformable for reduction of the chamber volume.

9. A diagnostic card for use with a card reader in sensing at least one component concentration of a fluid sample, comprising:
a card body
at least one component sensor located in a sensor region of the card body;
a sealed chamber defined in the card body outside the sensor region for containing a fluid, the chamber having a chamber wall sealing the chamber and being formed of a laminate of two opposed, plastic coated metal foil laminations bonded about their perimeter by a first heat seal made by melt bonding the plastic coatings of the laminations;
a fluid conduit for fluidically connecting the chamber with the sensor region, when the chamber is opened;
a valve seat in the card body and a valve for fluidically connecting the chamber to the fluid conduit, the valve including a valve body displaceably received in the valve seat and sandwiched between the laminations within the chamber, the valve body rupturing one of the laminations upon displacement of the valve body relative to the valve seat for rupturing the chamber wall of the sealed chamber at the connection to the fluid conduit without pressurization of the chamber, thereby opening the chamber; and
a delivery structure for forcing fluid from the chamber and into the fluid conduit, when the chamber contains fluid, the delivery structure being operable independently of the valve and being formed by a flexible portion of the chamber wall which flexible portion is deformable for reduction of the chamber by external application of a deforming force.

10. The diagnostic card of claim 9, wherein the valve body is a rupture plug and the valve seat is a plug receiving bore in the card body.

11. The diagnostic card of claim 10, wherein the plug and plug receiving bore include cooperating edges for rupturing the one of the laminations upon displacement of the plug in the plug receiving bore.

12. A diagnostic card for use with a card reader for sensing at least one component concentration of a fluid sample, comprising:
a planar card body having a pair of opposite planar external surfaces;
at least one sensor located in a sensor region of the card body;
a sample entry port in one of the external surfaces of the card for receiving a conduit for sample fluid infection;
a sample conduit within the card body for fluidically connecting the sample entry port to the sensor region; and
an adhesive gasket on the one external surface and surrounding the sample entry port for forming a liquid seal about the conduit, when inserted into the sample entry port.

13. The diagnostic card of claim 12, further comprising
a sealed chamber defined in the card body outside the sensor region for containing a fluid, the chamber having a chamber wall sealing the chamber; and
a fluid conduit for fluidically connecting the chamber with the sensor region, when the chamber is opened;
a valve for fluidically connecting the chamber to the fluid conduit, the valve having a structure for rupturing the chamber wall of the sealed chamber at the connection to the fluid conduit without pressurization of the chamber, thereby opening the chamber; and
a delivery structure for forcing fluid from the chamber and into the fluid conduit, when the chamber contains fluid, the delivery structure being operable independently of the valve and being formed by a flexible portion of the chamber wall which flexible portion is deformable for reduction of the chamber by external application of a deforming force.

14. The diagnostic card of claim 13, wherein the chamber is formed of a laminate of two opposed, plastic coated metal foil laminations bonded about their perimeter by a first heat seal made by melt bonding the plastic coatings of the laminations.

15. The diagnostic card of claim 14, wherein the heat seal has a width of at least 3 mm.

16. The diagnostic card of claim 13, wherein the card body includes a valve seat and the valve includes a valve body displaceably received in the valve seat, the valve rupturing the portion of the chamber wall upon displacement of the valve body relative to the valve seat.

17. The diagnostic card of claim 13, wherein the card body includes a valve seat and the valve includes a valve body displaceably received in the valve seat, the valve body being sandwiched between the laminations within the chamber, the valve rupturing one of the laminations upon displacement of the valve body relative to the valve seat.

18. The diagnostic card of claim 17, wherein the valve body is a rupture plug and the valve seat is a plug receiving bore in the card body.

19. The diagnostic card of claim 18, wherein the plug and plug receiving bore include cooperating edges for rupturing the one of the laminations upon displacement of the plug in the plug receiving bore.

* * * * *